US010682102B2

(12) United States Patent
Declerck (10) Patent No.: US 10,682,102 B2
(45) Date of Patent: Jun. 16, 2020

(54) SYSTEMS, ARTICLES OF MANUFACTURE, AND METHODS FOR MULTI-SCREEN VISUALIZATION AND INSTRUMENT CONFIGURATION

(71) Applicant: Fenwal, Inc., Lake Zurich, IL (US)

(72) Inventor: Frederic Declerck, Evanston, IL (US)

(73) Assignee: Fenwal, Inc., Lake Zurich, IL (US)

( * ) Notice: Subject to any disclaimer, the term of this patent is extended or adjusted under 35 U.S.C. 154(b) by 561 days.

(21) Appl. No.: 13/834,490

(22) Filed: Mar. 15, 2013

(65) Prior Publication Data

US 2014/0282181 A1   Sep. 18, 2014

(51) Int. Cl.
  *A61B 5/00*   (2006.01)
  *G16H 40/63*   (2018.01)
  *G06F 3/048*   (2013.01)

(52) U.S. Cl.
  CPC ............ *A61B 5/7445* (2013.01); *G06F 3/048* (2013.01); *G16H 40/63* (2018.01)

(58) Field of Classification Search
  CPC .... G06F 3/048; G06F 19/3406; A61B 5/7445
  See application file for complete search history.

(56) References Cited

U.S. PATENT DOCUMENTS

| 5,631,844 | A | * | 5/1997 | Margrey et al. ................. 702/22 |
| 5,788,688 | A | | 8/1998 | Bauer et al. |
| 6,055,487 | A | * | 4/2000 | Margery et al. ................. 702/84 |
| 6,192,320 | B1 | * | 2/2001 | Margrey et al. ................. 702/84 |
| 6,222,547 | B1 | * | 4/2001 | Schwuttke ............ G06T 11/206 345/419 |
| 7,145,457 | B2 | * | 12/2006 | Spitz ...................... G06K 17/00 340/286.02 |
| 2002/0032720 | A1 | * | 3/2002 | Nelson et al. ................. 709/201 |

(Continued)

FOREIGN PATENT DOCUMENTS

| EP | 2742961 A1 | 6/2014 |
| EP | 2778994 A1 | 9/2014 |
| WO | 2005057466 A2 | 6/2005 |

OTHER PUBLICATIONS

European Patent Office, "Search Report", issued in connection with European patent application No. 14000921.8-1952, dated Jul. 30, 2014, 10 pages.

(Continued)

*Primary Examiner* — Kieu D Vu
*Assistant Examiner* — Alvaro R Calderon, IV
(74) *Attorney, Agent, or Firm* — Becker Patent Law, LLC (57) ABSTRACT

Example systems and methods to visualize and manage medical device operations and troubleshooting are provided. Interface information from a plurality of medical devices is used to generate a visualization of the interface information from the one or more of the plurality of medical devices. Each medical device interface is represented by a miniature representation of the interface in the visualization. Each miniature representation is to convey information shown on the interface of the medical device. The visualization is provided to a user via a user interface at a remote control computer. The user interface is to facilitate user selection of a miniature representation to trigger display of a larger representation of the selected medical device interface information via the user interface.

16 Claims, 5 Drawing Sheets

(56) References Cited

U.S. PATENT DOCUMENTS

| | | | |
|---|---|---|---|
| 2002/0056672 A1* | 5/2002 | Lyle | G06F 3/0488 210/94 |
| 2002/0120676 A1 | 8/2002 | Biondi et al. | |
| 2002/0183585 A1* | 12/2002 | Willems | A61M 1/00 600/17 |
| 2003/0018289 A1* | 1/2003 | Ng et al. | 604/6.01 |
| 2003/0031992 A1* | 2/2003 | Laferriere et al. | 434/262 |
| 2003/0034885 A1* | 2/2003 | Catton | A61C 8/008 340/506 |
| 2003/0040835 A1 | 2/2003 | Ng et al. | |
| 2003/0233129 A1* | 12/2003 | Matos | 607/5 |
| 2004/0024384 A1 | 2/2004 | Novak | |
| 2005/0137653 A1* | 6/2005 | Friedman | A61B 5/0002 607/60 |
| 2007/0100520 A1* | 5/2007 | Shah | G07C 5/008 701/31.4 |
| 2007/0150810 A1* | 6/2007 | Katz | G06F 3/0481 715/229 |
| 2007/0162860 A1* | 7/2007 | Muralidharan et al. | 715/736 |
| 2007/0208833 A1* | 9/2007 | Bucholz | 709/220 |
| 2007/0234219 A1* | 10/2007 | Bhattaru | 715/744 |
| 2007/0251835 A1* | 11/2007 | Mehta | A61B 5/14532 205/783 |
| 2007/0253021 A1* | 11/2007 | Mehta | A61B 5/0002 358/1.15 |
| 2007/0254593 A1* | 11/2007 | Jollota | A61B 5/14532 455/67.11 |
| 2007/0255116 A1* | 11/2007 | Mehta | A61B 5/0002 600/300 |
| 2007/0258395 A1* | 11/2007 | Jollota | A61B 5/14532 370/310 |
| 2008/0062167 A1* | 3/2008 | Boggs | G06F 17/5004 345/419 |
| 2008/0115146 A1* | 5/2008 | Claus et al. | 719/313 |
| 2009/0055735 A1* | 2/2009 | Zaleski | G06F 19/3406 715/700 |
| 2009/0295918 A1* | 12/2009 | Horovitz | H04N 7/181 348/143 |
| 2010/0049542 A1* | 2/2010 | Benjamin | G06F 19/366 705/2 |
| 2010/0223574 A1* | 9/2010 | Wang et al. | 715/778 |
| 2011/0006876 A1* | 1/2011 | Moberg | G06F 19/3406 340/3.2 |
| 2011/0172550 A1* | 7/2011 | Martin et al. | 600/523 |
| 2011/0201911 A1* | 8/2011 | Johnson et al. | 600/365 |
| 2011/0267418 A1* | 11/2011 | Galindo et al. | 348/14.04 |
| 2012/0038651 A1* | 2/2012 | Case | G06Q 10/087 345/440 |
| 2012/0185267 A1* | 7/2012 | Kamen | G06Q 50/22 705/2 |
| 2012/0192077 A1* | 7/2012 | Castellani et al. | 715/740 |
| 2012/0245745 A1* | 9/2012 | Vandevelde et al. | 700/286 |
| 2012/0254792 A1* | 10/2012 | Husoy | G06F 3/0481 715/782 |
| 2012/0278759 A1* | 11/2012 | Curl | G06F 19/327 715/804 |
| 2013/0055166 A1* | 2/2013 | Stinger | G06F 17/30592 715/853 |
| 2013/0176230 A1* | 7/2013 | Georgiev et al. | 345/173 |
| 2013/0191513 A1* | 7/2013 | Kamen | G06F 19/322 709/219 |
| 2013/0297330 A1* | 11/2013 | Kamen | G06F 19/323 705/2 |
| 2013/0298026 A1* | 11/2013 | Fitzpatrick | 715/723 |
| 2013/0317753 A1* | 11/2013 | Kamen | G06F 19/3412 702/19 |
| 2013/0332882 A1* | 12/2013 | Laycock | G06F 9/4443 715/783 |
| 2014/0018779 A1* | 1/2014 | Worrell et al. | 606/1 |
| 2014/0089821 A1* | 3/2014 | Rios et al. | 715/761 |
| 2014/0237304 A1* | 8/2014 | Lai | G06F 11/0742 714/57 |
| 2014/0359752 A1* | 12/2014 | Swaminathan | 726/16 |

OTHER PUBLICATIONS

Communication in EP App. No. 14000921.8, dated May 12, 2016, 7 pages.
Samson & Partner Response Letter in EP App. No. 14000921.8, Sep. 22, 2016, 17 pages.
Samson & Partner Response Letter in EP App. No. 14000921.8, Mar. 17, 2015, 21 pages.

* cited by examiner

SYSTEMS, ARTICLES OF MANUFACTURE, AND METHODS FOR MULTI-SCREEN VISUALIZATION AND INSTRUMENT CONFIGURATION

CROSS-REFERENCE TO RELATED APPLICATIONS

[Not Applicable].

FIELD OF THE DISCLOSURE

The present disclosure relates generally to systems, articles of manufacture, and methods for remote visualization and configuration of medical devices. More particularly, the present disclosure is directed to systems, articles of manufacture, and methods for multi-screen visualization and medical instrument configuration.

BACKGROUND

Increasingly, medical devices are becoming electronic or involve an electronic or software component. Electronic devices, distributed facilities, and scattered patients make training, treatment, and troubleshooting difficult. Operators and administrators may also introduce inefficiencies in their operation and management of medical devices due to a lack of information and access.

Unfortunately, blood centers and other medical facilities have lacked innovative methods of managing operations and data, and have failed to discover or implement ways to drive further enhancements in areas such as efficiency, productivity, recruitment of donors, and safety.

SUMMARY

The present disclosure is directed to systems and methods to visualize and manage medical device operations and troubleshooting.

Certain examples provide a medical device interface visualization system including a processor. The example processor is configured to implement a communication channel, a remote controller, and a user interface. The example communication channel is to communicate with a plurality of medical devices to receive interface information for one or more of the plurality of medical devices. The example remote controller is to generate a visualization of the interface information from the one or more of the plurality of medical devices. The example user interface is to provide the visualization of the medical device interface information to a user. Each medical device interface is represented by a miniature representation of the interface in the visualization. Each miniature representation is to convey information shown on the interface of the medical device. The user interface is to facilitate user selection of a miniature representation to trigger display of a larger representation of the selected medical device interface information via the user interface.

Certain examples provide a tangible computer readable storage medium including a set of instructions to be executed by a processor. The instructions, when executed, implement a method to facilitate visualization and troubleshooting of a plurality of medical devices. The example method includes communicating with a plurality of medical devices to receive interface information for one or more of the plurality of medical devices. The example method includes generating a visualization of the interface information from the one or more of the plurality of medical devices via a user interface. The example method includes providing the visualization of the medical device interface information to a user. Each medical device interface is represented by a miniature representation of the interface in the visualization. Each miniature representation is to convey information shown on the interface of the medical device. The example method includes facilitating user selection of a miniature representation to trigger display of a larger representation of the selected medical device interface information via the user interface.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

The following description discloses examples of systems, articles of manufacture, and methods for monitoring, managing, and troubleshooting multiple medical device instruments, such as blood collection and processing devices, other apheresis devices, infusion pumps, drug delivery pumps, and/or other medical devices. The present disclosures are not intended to limit the broad aspects of the invention.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements is hereby expressly defined to include a tangible medium such as a memory, a digital video disc (DVD), compact disc (CD), BLU-RAY™, etc. storing the software and/or firmware.

The present disclosure is directed to systems and methods for managing medical devices, such as blood processing and/or drug delivery instruments and associated procedures. This is stated in a broad sense which is intended to include further use and manipulation of data associated with blood processing procedures and the instruments, soft goods, donors, collected products, administrators, operators and facilities related to such procedures. For purposes of the present disclosure, the term "facility" or "center" will be used to refer to a location capable of biological fluid collection and/or processing via one or more collection or processing instruments, as well as a location capable of fluid (e.g., drug) infusion and/or processing via one or more infusion pumps or other such instruments. The facility and/or center can be a fixed and/or mobile facility/center, for example. Also, as used herein, the term "blood processing procedures" is intended to refer to any type of biological fluid collection, regardless of whether it includes the collection of blood or blood components.

In some examples, each facility includes a plurality of separately operable medical instruments, a facility administrator and a plurality of facility operators for administration of one or more procedures involving one or more donors and/or patients. The system generally includes a system server linked to the collection instruments.

The system server can include a communication protocol that facilitates communication between the system server and each of the plurality of medical instruments, and further can be linked to a headquarters (HQ) server, for an organization having more than one collection facility, as well as to a system of an outside entity, such as Fenwal, Inc., of Lake Zurich, Ill., the supplier of instruments and soft goods, such as the collection kits used in the collection procedures.

The system server receives information or data, generally referred to hereafter collectively as "data", relating to collections and/or infusions using one or more of a plurality of medical instruments. The system server also can receive data associated with the placement, maintenance and status or other issues relating to the collection instruments. Data also can be received with respect to donors, patients, administrators, operators, products collected, or related information, from mobile data transmission devices in the form of personal digital assistants (PDA's), such as a PALM PILOT™ by Palm, a PPT 2800 mobile computer by Symbol Technologies, or other handheld devices having scanning, bar code reading and/or key entry capability, or via "smart" devices, such as a radio frequency identifier (RFID) tag, smart card or comparable device to which data can be written and from which such data can be retrieved, or from input terminals, such as in the form of a desk top computer. The system server is adapted to store data in the system server memory and can be adapted to interact with outside network systems, such as a corporate system that is capable of pooling data from multiple collection facilities, systems of suppliers, such as Fenwal, Inc., or a system associated with other entities with which it can be desirable to link the system server.

The disclosed systems, articles of manufacture, and methods can be incorporated into an existing facility's system via an upgrade to existing hardware and software, or can be implemented in an entirely new facility that is equipped with devices more particularly designed for compatibility with the disclosed systems and methods. The present system provides a data connection between a collection facility's data management system, laboratory instruments, including, but not limited to, existing blood and blood component collection instruments, such as for example the AUTOPHERESIS-C® and/or AURORA® plasmapheresis instrument which are supplied by Fenwal, Inc., the Fenwal CS-3000®, AMICUS®, and/or ALYX® separators, also from Fenwal, Inc., and the instruments generally described in PCT Publication No. WO 01/17584, U.S. Pat. Nos. 5,581,687, 5,956,023, and 6,256,643, and biological treatment instruments, such as for example the pathogen inactivation instruments described in U.S. Pat. No. 7,025,877, which are all incorporated herein by reference.

Some example systems described herein lend themselves to automated tracing and/or tracking of several aspects of interactions with donors and/or patients and utilization of a facility's assets. Numerous high level manipulations and uses of data are provided via integration of data from facility instruments, donors, administrators, operators, soft goods, and collected products. Recordation of data and event reporting can be further automated for strategic purposes, such as for enhanced safety, efficiency, productivity, profitability, value analysis, regulatory compliance, etc.

In certain examples, a medical device, such as a plasmapheresis system, supports two-way, wireless data communication designed to eliminate manual steps and increase operator and donor satisfaction. The example system includes interactive touch-screen display with intuitive menus and icons, delivers productivity reports, and enables remote procedure set-up and paperless documentation, for example. The example system also offers custom features that improve work flow and help assure a successful collection. Intuitive on-screen instructions simplify training for operators and provide troubleshooting assistance. A display, such as a liquid crystal display (LCD) allows donors themselves to see how their donation is progressing.

The example system can support remote procedure set up, paperless documentation, and 21 CFR Part 11 compliance when combined with data management system (e.g., Fenwal DXT® Relay) software and a plasma center's donor management software. With remote procedure set up, the example system can be automatically programmed based on donor registration information. These features help assure data accuracy, documentation compliance, and streamline the set-up procedure, for example.

In certain examples, data management system provides plasma center professionals with easy-to-read, on-demand reports that aggregate donor and procedure data from multiple apheresis and/or infusion systems at different locations. The reports track specific performance indicators and can be used to identify opportunities for improvement and training, for example. Standard reporting templates can be provided to drive reduction of operating costs. Additionally, reports can be customized to track specific performance indicators.

In certain examples, barcode scanning can be used to facilitate donor/patient identification, operator identification, soft goods verification, etc. Improved alarm notification system and new troubleshooting graphics help operators resolve issues quickly. Data management solutions provide access to data anytime, anywhere. Data resides on the user's network, and wireless and Ethernet device data export capabilities are provided. For example, data resides securely within a blood center network and can be easily accessed at any time by authorized blood center personnel. Data can be collected from, exchanged with, and/or processed by donor centers, mobile drives, etc. For example, reports can be gathered from devices across one or more locations and can include: procedure summary reports by device and/or by operator, number of products collected and/or dispensed per procedure, alarms by device and/or by operator, event tracking, daily utilization summary, etc.

To simplify implementation and reduce costs for blood centers, the data management relay software uses an open-architecture approach to integrate seamlessly with blood center management systems. Paperless documentation and remote procedure setup can be facilitated through an exchange between an apheresis or other medical device and the data management system.

Certain examples provide a multiple screen visualizer for a plurality of blood processing and/or other (e.g., infusion pump, etc.) instruments. Using the visualizer, a user (e.g., a blood center supervisor, clinical administrator, etc.) can quickly visualize the actual displays of instruments running in the facility.

The visualizer allows a supervisor to see every screen of the apheresis and/or other medical device instruments in a particular location or set of locations under the guidance of the supervisor (e.g., a hospital, clinic, blood center, set of blood centers, etc.). The screens of the individual devices are displayed via an overview display as thumbnails and/or other representations smaller than the actual screen size of the respective device. Upon clicking, touching, or otherwise selecting a mini-screen representation on the visualizer display, the application shows the actual instrument screen on a larger scale. Navigation, such as sliding fingers right or left on the visualizer display, selecting a left or right or page indicator, etc., allows the user to move to a previous or next or particular page number screen, for example. Via the visualizer, a supervisor can quickly see the status of every screen for which he or she is responsible.

Figure 1:
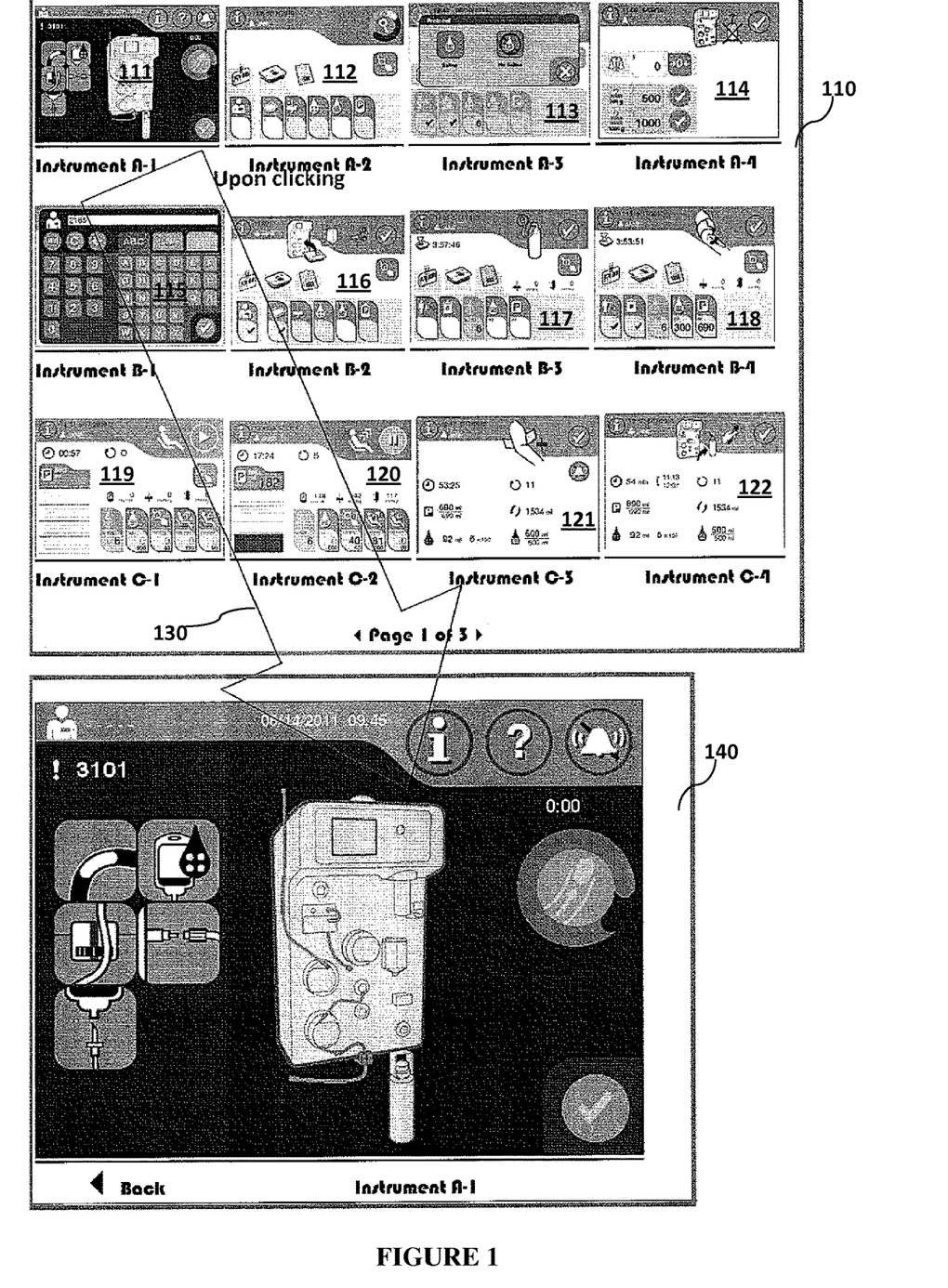
FIG. 1 illustrates an example visualizer including a plurality of miniature screen representations of instruments.

FIG. 1 illustrates an example visualizer 110 including a plurality of miniature screen representations 111-122 of instruments A-1 through C-4. As illustrated in the example of FIG. 1, while the plurality of instruments may be of the same type, instruments can also be of varying types (e.g., apheresis machines, plasmapheresis machines, infusion pumps, drug delivery systems, etc.). Each of the representations 111-122 provides an instrument interface screen capture and/or live feed from the instrument interface A-1 to C-4, for example.

Clicking on or otherwise selection a screen 111-122 triggers display of the selected instrument A-1-C-4 screen 140 in full. As illustrated in the example of FIG. 1, selecting a screen representation 111 for instrument A-1 transitions the visualizer display from the multi-screen view 110 to a single instrument A-1 view 140 indicated by the transition arrow 130. By reviewing the instrument A-1 screen 140, a supervisor or other user can identify an error, alert, alarm, etc., at the instrument A-1. The supervisor can then troubleshoot remotely, troubleshoot at the instrument, help an operator at the instrument troubleshoot, etc.

In certain examples, a user touch or gesture on a touch-screen providing the visualizer 110 allows the user to navigate between multiple pages or views of instrument representations. As shown in FIG. 1, three pages of instrument screens are provided, and sliding left or right allows the user to see a previous or next screen. A back button can be provided to return to a main screen, such as the multiple screen display 110, for example. Thus, a supervisor can monitor each instrument in a facility and/or other group.

For example, a plasma center includes multiple levels and only one manager. The visualizer 110 provides a representation, such as a snapshot, preview, thumbnail, and/or other indicator, of every instrument in the center. There may be several pages of information depending upon a number of instruments in the center. Movement between screens can be facilitated by scrolling on the user interface to go from one page to another, for example.

In certain examples, a color indication (e.g., black, red, orange, yellow, etc.) provides a visual representation or cue of a problem or error with an instrument to provoke the center manager's interest. An operator may not have the right or permission to continue beyond an alarm, so the manager or supervisory may need to step in and assist to troubleshoot, reset, etc., the machine.

Thus, certain examples facilitate instrument monitoring for problems to help expedite and enable troubleshooting by a supervisor, manager, and/or other user to assist an instrument operator. Driven by individual devices and/or a remote controller, such as a tablet computer, desktop personal computer, laptop, smartphone, etc., an individual medical device screen can be captured (e.g., as a screenshot, live feed, etc.), saved, and sent to the remote controller for display (e.g., via the visualizer 110 and full screen 140 display). In certain examples, no control is provided to the user via the remote controller, just information. Alternatively or in addition, the remote controller can enable a user (e.g., a manager, supervisor, administrator, etc.) can send a message to an instrument operator via the instrument to guide the operator in troubleshooting (e.g., flashing lights, pop-up message, intercom, etc.).

In certain examples, if there are multiple pages of instrument "mini-screens" and an alert exists for an instrument on a page other than the page currently displayed, the interface can automatically move to the page having the alert and/or otherwise adjust the display to show the page of the alert (e.g., move the alert to the page currently displayed, etc.). If there are multiple alarms, the interface can default to show the page with a highest priority alarm, order the instruments with alarms on the displayed page in order of importance/priority, timing, etc. For example, alarms can be distinguished according to priority. If more than one high priority alarm is present, whichever alarm came first is prioritized first, for example.

Figure 2:
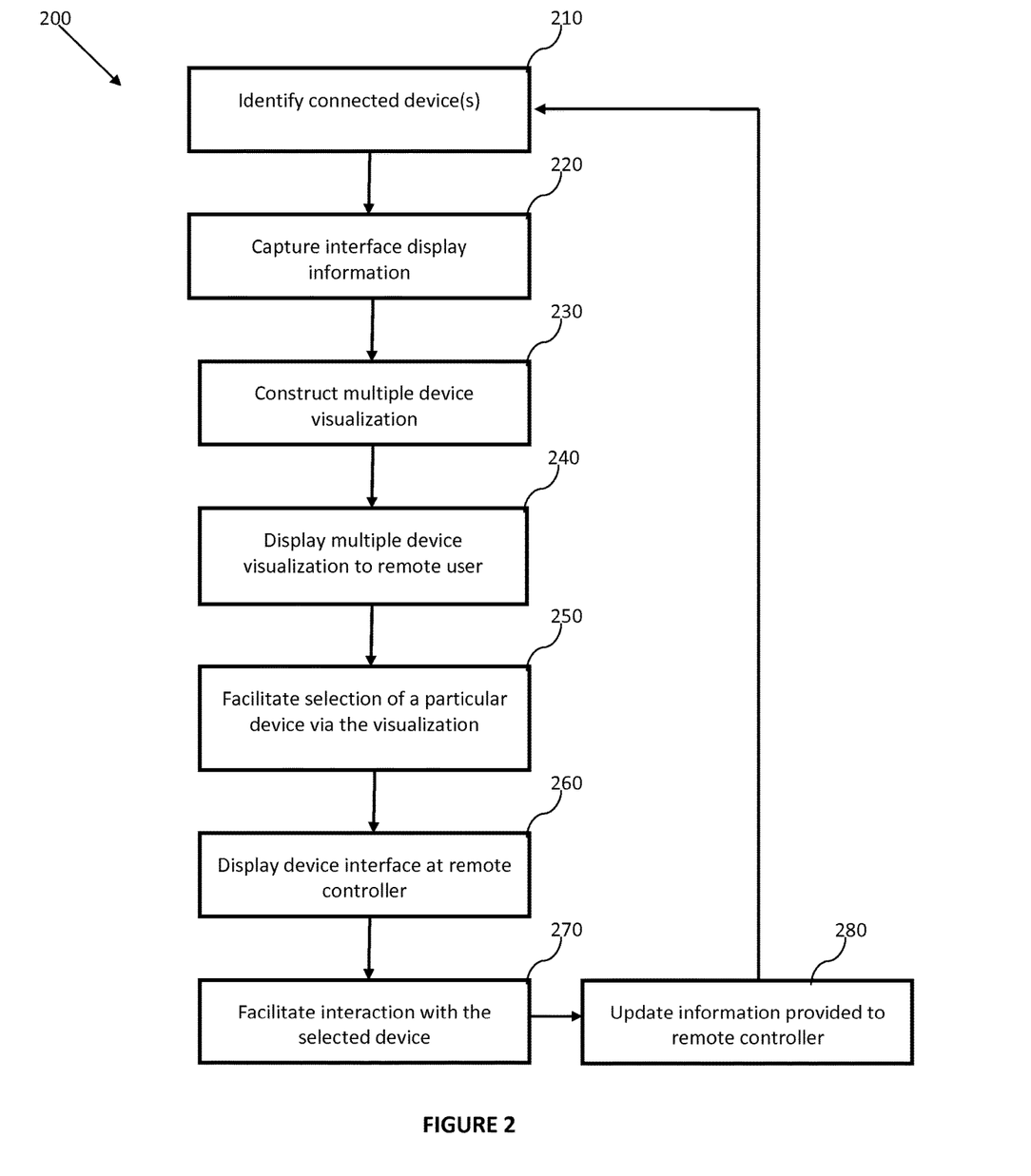
FIG. 2 illustrates a flow diagram of an example method to visualize medical device status for a plurality of medical devices via a single interface.

FIG. 2 illustrates a flow diagram of an example method 200 to visualize medical device status for a plurality of medical devices via a single interface. At block 210, connected medical devices are identified. For example, the medical devices can broadcast or unicast their presence to a remote controller and/or the remote controller can seek out connected medical devices. For example, a tablet computer running a remote control visualizer program can ping instruments, such as apheresis instruments, infusion pumps, delivery instruments, etc., in a facility to determine which ones can communicate with the tablet to allow visualization of their current interface displays.

At block 220, connected medical device(s) are accessed to capture user interface and/or other display/screen information. For example, a screen capture can be taken by a plasmapheresis instrument and sent to the remote controller tablet to be included in a multi-instrument mini-screen representation visualization. Error, alarm, and/or other alert information can be provided as well as the interface information, for example.

At block 230, based on received information from the connected devices, a multiple device interface visualization is constructed at the remote controller. For example, multiple screen captures are organized in a visualization interface for view and interaction via a tablet computer, smartphone, etc. The screen captures and/or live feeds can be organized according to proximity, priority, urgency, and/or other organizational criterion, for example.

At block 240, the multiple device visualization is displayed to a remote user. For example, the multi-screen visualizer is provided to a supervisor, manager, administrator, etc., via a mobile device, such as a tablet, smartphone, laptop, etc. The user can view reduced or miniaturized representations of the various device interfaces via the multi-device view. For example, the user can view screenshot thumbnails, miniature live feeds of user interface displays, etc. Data such as device identifier (ID), device status, soft goods status (e.g., amount of drug or other fluid dispensed/available, filter status, tubing availability, collection bag availability, other disposable kit status or inventory information, etc.), procedure progress, alerts or alarms, information notice, etc., can be provided through and/or in conjunction with the device interface representation, for example. Such information can be used for troubleshooting, re-ordering, reporting, analytics, etc.

At block 250, selection of a particular device representation is facilitated via the multi-device visualization at the remote controller. For example, a user can select a mini-screen thumbnail via the multi-device visualizer on a tablet, smartphone, laptop, etc., by touching the mini-screen representation, moving a pointer or cursor of the mini-screen representation, selecting the representation from a list, etc.

At block 260, the selected device interface is displayed via the remote controller. For example, selection of a miniature screen representation in a visualizer view launches a full-screen or other larger view of the particular selected device interface. The interface view can be a still screen capture of the device's interface, a live feed of the device interface, etc. In certain examples more information can be provided in the full interface view versus the miniature representation view.

At block 270, interaction between the user and the selected device is facilitated. For example, the user (e.g., a manager, supervisor, admin, etc.) can remotely troubleshoot the instrument via the interface feed. As another example, the user can contact an operator of the medical device to guide the operator through local troubleshooting of the device based on information provided through the interface view (e.g., screen capture, live feed, supporting information, etc.). As another example, the user can visit the device in question and trouble shoot the device while reviewing the information provided on the interface (e.g., via a tablet, smartphone, laptop, or other mobile computing device).

At block 280, information provided to the remote controller is updated. For example, individual connected devices can be polled by the remote controller, devices can push updates to the remote controller, devices can be added, devices can be removed, alerts/alarms/other information can be updated for a device representation as problems are fixed and/or new problems arise, etc.

Additionally, certain examples provide quick setup of one or more instruments in a mode outside of a normal operational mode (e.g., administrative and/or service modes). Center administrators can quickly set up instruments from a remote device (e.g., a tablet computer, handheld computer, smart phone, laptop, etc.).

This feature can be used to set administrator and/or service settings. The application allows a user to set parameters from a remote device by taking over the instrument's screen. That way an administrator does not have to physically access every device in his or her purview.

Figure 3:
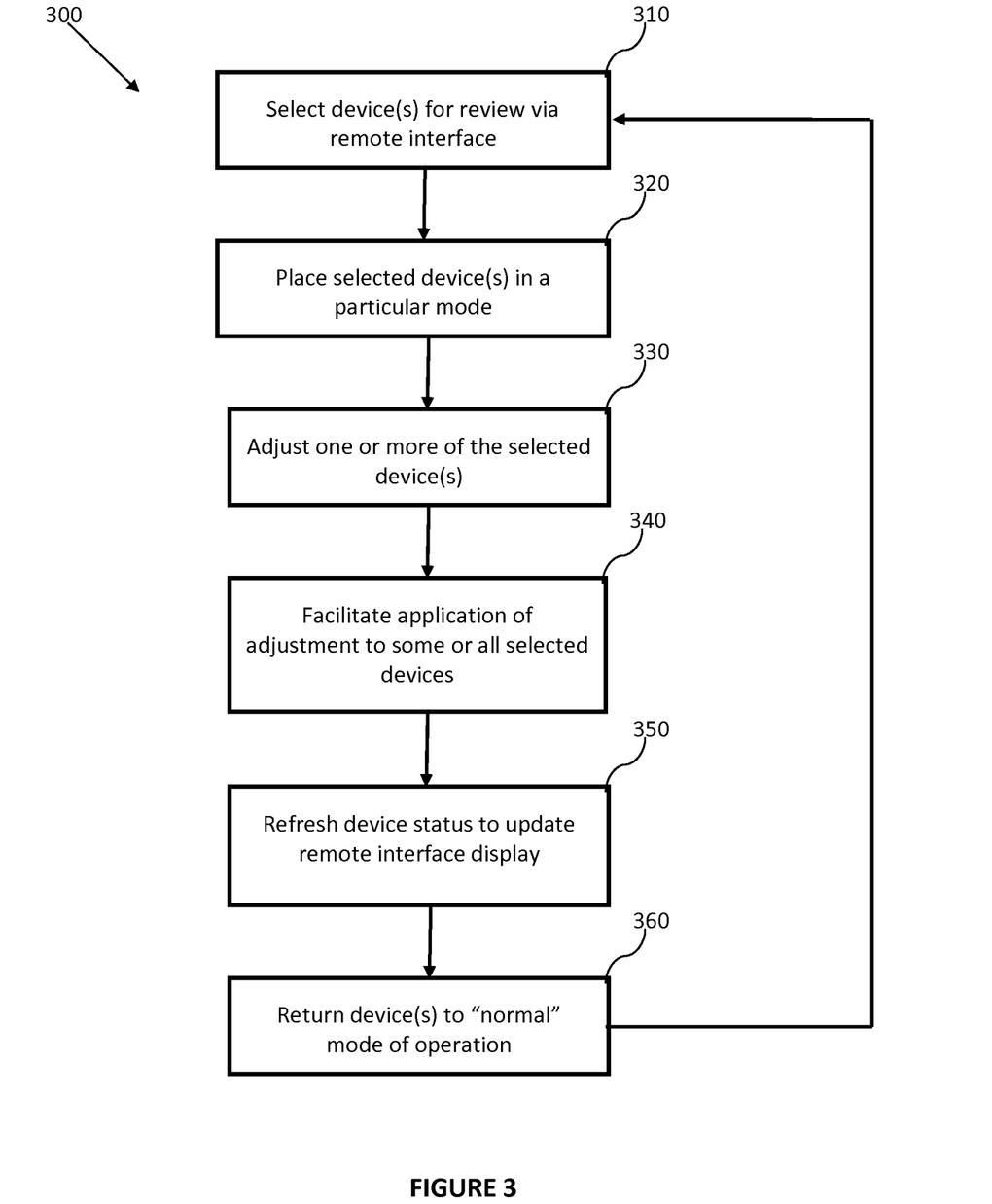
FIG. 3 illustrates a flow diagram of an example method to remotely control one or more medical devices.

FIG. 3 illustrates a flow diagram of an example method 300 to remotely control one or more medical devices. The method 300 allows a user to access an admin and/or service mode. Upon accessing either of these modes, the user takes over control of a specific instrument screen. The user can set one or more parameters at the selected instrument from a remote device. Thus, an administrator can set parameter(s) for some or all of his or her instruments from the remote device.

Rather than manually access an instrument to select a mode through a menu on the instrument interface (e.g., admin mode) or manually flip a switch while the instrument is turned off (e.g., service mode), a user can cause a device to switch modes remotely from a visualization interface. In certain examples, a safety mechanism is provided to make sure the instrument cannot switch during a procedure. For example, in three clicks, a user can place an instrument in admin mode or service mode by sending a remote command to one or more instruments depending upon instrument status. A user can then troubleshoot or otherwise service, reconfigure, update, upgrade, etc., one or more connected medical devices from a centralized remote visualization/configuration interface, for example. In certain examples, update/upgrade is tied to an agreement, service contract, license, etc.

At block 310, one or more medical devices are selected for review via a remote interface. For example, mini-screen representations, instrument icons, instrument names, etc., are provided for display and user selection via a user interface on a computing device such as a laptop computer, tablet computer, smartphone, etc. One or more devices can be selected by touch, cursor positioning, typing name(s), etc.

At block 320, the one or more selected devices are accessed to place the device(s) into a particular mode. For example, a command is sent one or more of the selected devices to place the device(s) into a service mode, an administrative mode, etc. A single command can be multicast to a plurality of devices, different commands can each be unicast to a particular device, etc.

At block 330, an adjustment can be made to each of the one or more selected device(s). For example, each of the device(s) can be updated, upgraded, restarted, locked, troubleshot, etc., depending upon the device, mode, and user instruction. At block 340, the user can specify whether an adjustment is to be made to a single selected device and/or multiple selected devices. For example, an update may be applied to all selected devices (e.g., of a given type), while troubleshooting or reset may only apply to one selected instrument. For example, the user may be given an option to "apply setting to all devices" and/or may be able to view listing(s) or page(s) of devices where the user can select which instruments he or she is intending to configure.

At block 350, device status can be refreshed to provide an update to the user via the remote interface. The user can then take further action, if warranted or desired. At block 360, the device(s) are returned to a "normal" mode of operation. For example, the service or admin mode is closed so that operation can resume and so that the operator or patient/donor cannot make restricted adjustments to the device. As another example, the device may be restarted so that changes take effect and the device starts in "normal" mode.

Figure 4:
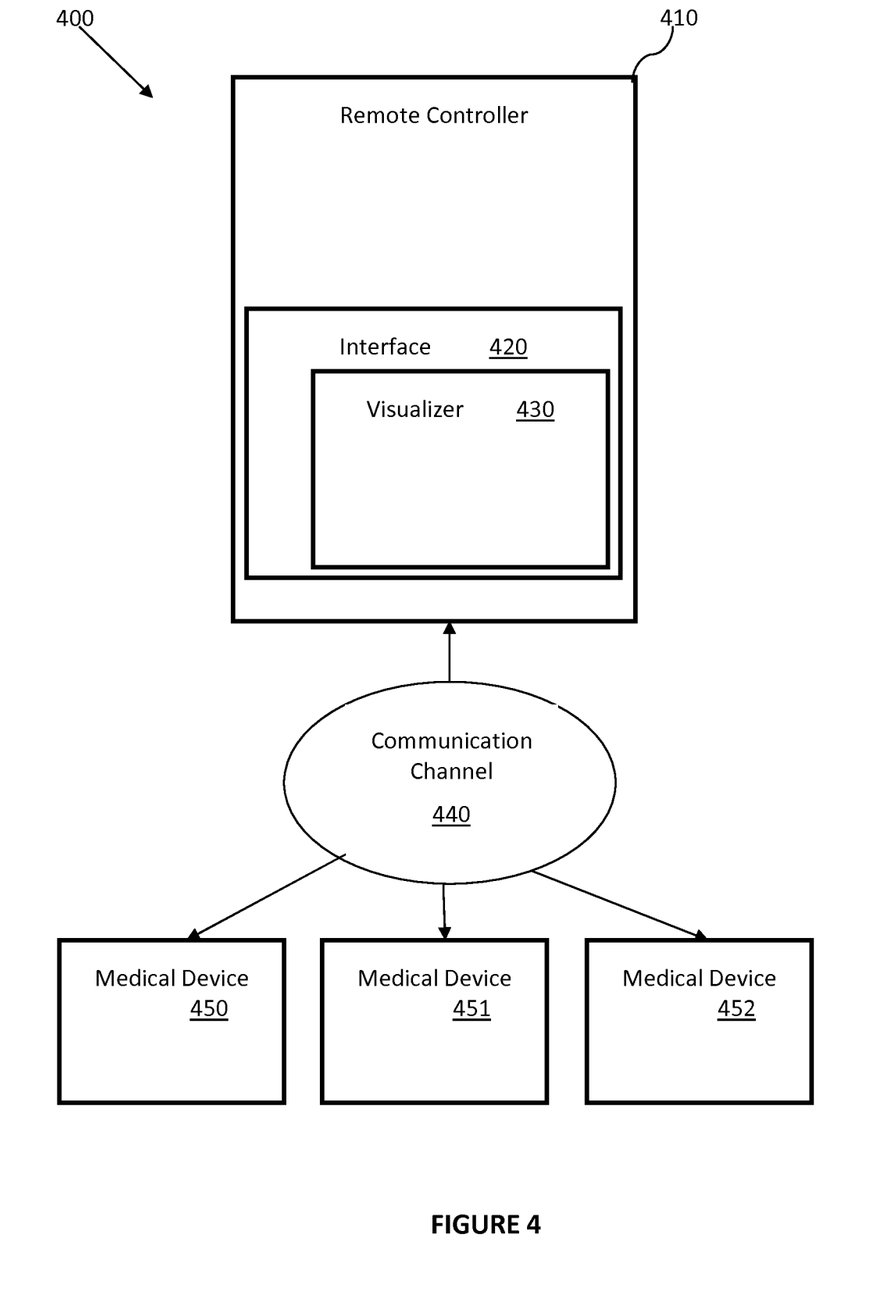
FIG. 4 illustrates components of an example system to facilitate remote monitoring, troubleshooting, and maintenance of a plurality of medical devices.

FIG. 4 illustrates components of an example system 400 to facilitate remote monitoring, troubleshooting, and maintenance of a plurality of medical devices, such as blood collection and processing instruments, infusion pumps, drug delivery systems, etc. The example system 400 includes a remote controller 410 including an interface 420 providing a visualizer 430 for visualization of a plurality of connected devices 450-453. Via a communication channel 440, such as a direct cable connection, wireless network, near field communication, BLUETOOTH® communication, infrared communication, local area network (LAN) communication, wide area network (WAN) communication, etc., the remote controller 410 communicates with the connected devices 450-453 to gather interface information and/or other operational data and to interact with the devices 450-453 for analysis, troubleshooting, updating, etc.

Thus, certain examples can provide enhanced value at multiple levels within a business based on improved operational and data management with reduced manual data collection and/or improved data manipulation. Certain examples lessen an individual device operator's intervention with the medical device and allow for an enhanced data management system for facilities. By using a remote viewer and controller to monitor, troubleshoot, report on, and maintain devices, the burden on managers and operators can be lessened. The operator can reduce or eliminate manual entry of parameters and other configuration information into a medical device and can instead rely on the supervisor or manager to solve or help solve issues remotely. In addition, the manager or supervisor can streamline his or her approach to responding to problems, upgrading equipment, reconfiguring equipment, etc.

Certain examples provide a comprehensive view to help improve operational performance at and/or across blood collection facilities. The system can be used, for example, in a donor center that manages multiple instruments that collect and/or process blood components. The visualizer and remote controller provide tools and guidance for a donor center to operate more efficiently by utilizing information available from instrumentation that collects and/or processes blood components.

Figure 5:
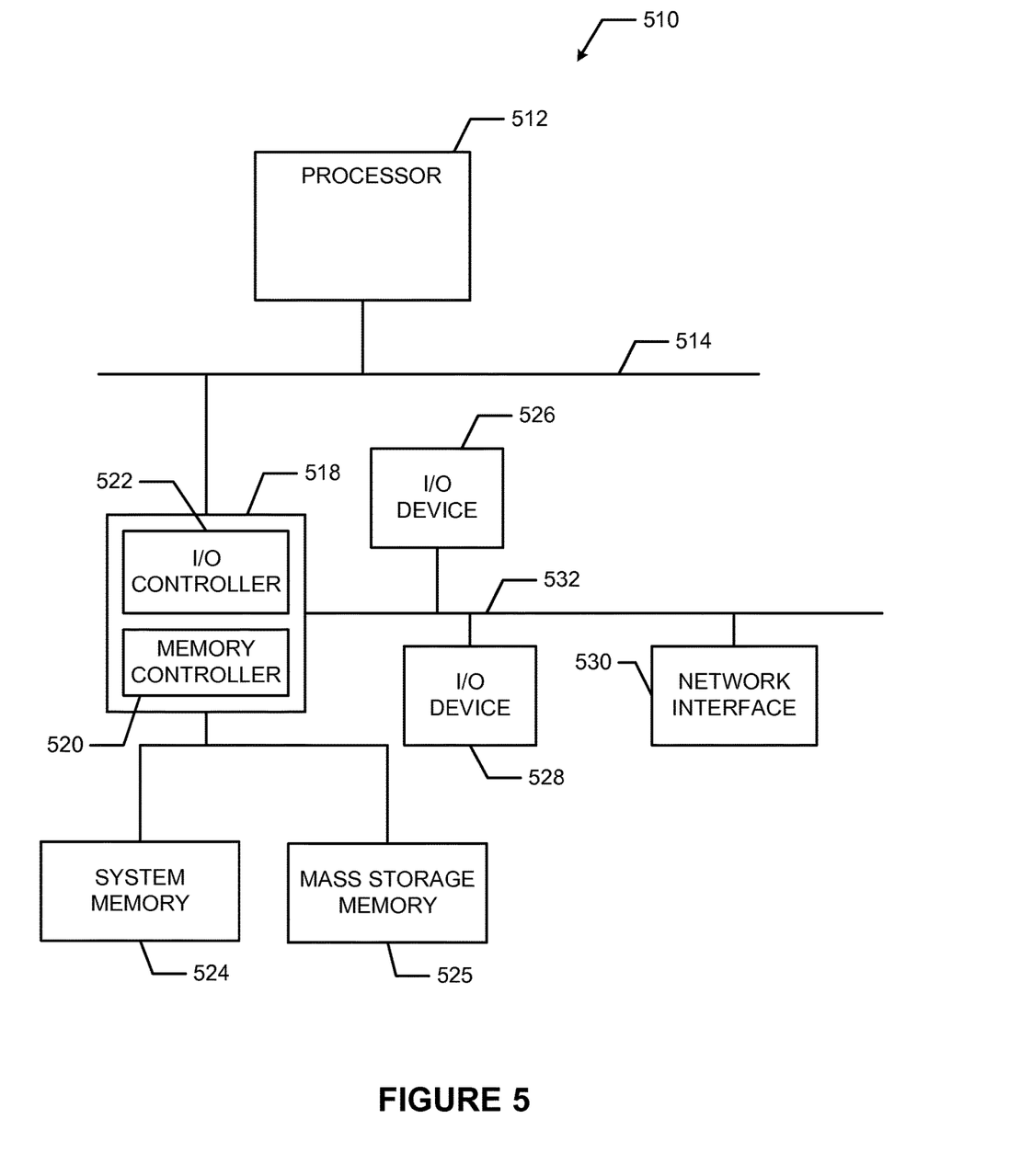
FIG. 5 is a block diagram of an example processor system that can be used to implement systems, articles of manufacture, and methods described herein.

FIG. 5 is a block diagram of an example processor system 510 that can be used to implement systems, articles of manufacture, and methods described herein. As shown in FIG. 5, the processor system 510 includes a processor 512 that is coupled to an interconnection bus 514. The processor 512 can be any suitable processor, processing unit, or microprocessor, for example. Although not shown in FIG. 5, the system 510 can be a multi-processor system and, thus, can include one or more additional processors that are identical or similar to the processor 512 and that are communicatively coupled to the interconnection bus 514.

The processor 512 of FIG. 5 is coupled to a chipset 518, which includes a memory controller 520 and an input/output ("I/O") controller 522. As is well known, a chipset typically provides I/O and memory management functions as well as a plurality of general purpose and/or special purpose registers, timers, etc. that are accessible or used by one or more processors coupled to the chipset 518. The memory controller 520 performs functions that enable the processor 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode ("ATM") device, an 802.11 device, a DSL modem, a cable modem, a cellular modem, etc. that enables the processor system 510 to communicate with another processor system.

While the memory controller 520 and the I/O controller 522 are depicted in FIG. 5 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 510 of FIG. 5). When any of the appended claims are read to cover a purely software and/or firmware implementation, at least one of the components is hereby expressly defined to include a tangible medium such as a memory, DVD, CD, etc. storing the software and/or firmware.

FIGS. 2 and 3 include flow diagrams representative of machine readable and executable instructions or processes that can be executed to implement the example systems, apparatus, and article of manufacture described herein. The example processes of FIGS. 2 and 3 can be performed using a processor, a controller and/or any other suitable processing device. For example, the example processes of FIGS. 2 and 3 can be implemented in coded instructions stored on a tangible medium such as a flash memory, a read-only memory (ROM) and/or random-access memory (RAM) associated with a processor (e.g., the processor 512 of FIG. 5). Alternatively, some or all of the example processes of FIGS. 2 and 3 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 2 and 3 can be implemented manually or as any combination(s) of any of the foregoing techniques, for example, any combination of firmware, software, discrete logic and/or hardware. Further, although the example processes of FIGS. 2 and 3 are described with reference to the flow diagrams of FIGS. 2 and 3, other methods of implementing the processes of FIGS. 2 and 3 can be employed. For example, the order of execution of the blocks can be changed, and/or some of the blocks described can be changed, eliminated, sub-divided, or combined. Additionally, any or all of the example processes of FIGS. 2 and 3 can be performed sequentially and/or in parallel by, for example, separate processing threads, processors, devices, discrete logic, circuits, etc.

As used herein, the term tangible computer readable medium is expressly defined to include any type of computer readable storage and to exclude propagating signals. Additionally or alternatively, the example processes of FIGS. 2 and 3 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

One or more of the components of the systems and/or steps of the methods described above can be implemented alone or in combination in hardware, firmware, and/or as a set of instructions in software, for example. Certain embodiments can be provided as a set of instructions residing on a computer-readable medium, such as a memory, hard disk, DVD, or CD, for execution on a general purpose computer or other processing device. Certain embodiments of the present invention can omit one or more of the method steps and/or perform the steps in a different order than the order listed. For example, some steps can not be performed in certain embodiments of the present invention. As a further example, certain steps can be performed in a different temporal order, including simultaneously, than listed above.

Certain embodiments include computer-readable media for carrying or having computer-executable instructions or data structures stored thereon. Such computer-readable media can be any available media that can be accessed by a general purpose or special purpose computer or other machine with a processor. By way of example, such computer-readable media can include RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory can include read only memory (ROM) and random access memory (RAM). The computer can also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes can be made and equivalents can be substituted without departing from the scope of the invention. In addition, many modifications can be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical device interface system comprising a processing circuit configured to implement:
    a communication channel configured to communicate with a plurality of medical devices, the medical devices selected from a group consisting of a blood processing instrument, an infusion pump, and a drug delivery system, to receive interface screen data for each of the plurality of medical devices;
    a processing component configured to generate a first screen comprising representations of the interface screen data from the plurality of medical devices, each representation to convey information shown on a respective interface screen of a corresponding medical device, to receive an indication of user selection of one of the representations displayed on the first screen, and to generate a larger screen representation of the interface screen data of the selected representation, the processing component further configured to receive through the communication channel an indication of an alert or alarm associated with one of the medical devices and to generate a corresponding indication of the alert or alarm on one of the first screen and the larger screen, wherein the representations of the interface screen data from the plurality of medical devices are miniature screen shots or live feeds of screens displayed on the medical devices.

2. The medical device interface system of claim 1, wherein both the first screen and the larger screen convey indicators of the alert or alarm with respect to one of the plurality of medical devices.

3. The medical device interface system of claim 1, wherein the first screen comprises an indication of a status of a disposable kit for the medical device.

4. The medical device interface system of claim 1, wherein the first screen comprises an indication of an amount of drug dispensed by a medical device.

5. The medical device interface system of claim 1, wherein the processing circuit is further configured to implement a command component configured to multi-cast a single command over the communication channel to place a plurality of the medical devices into a mode.

6. The medical device interface system of claim 1, wherein the larger screen representation comprises more data than the representation on the first screen for a particular medical device.

7. A medical device interface system comprising a processing circuit configured to implement:
   a communication channel configured to communicate with a plurality of medical devices, the medical devices selected from a group consisting of a blood processing instrument, an infusion pump, and a drug delivery system, to receive interface screen data for each of the plurality of medical devices;
   a processing component configured to generate a first screen comprising representations of the interface screen data from the plurality of medical devices, each representation to convey information shown on a respective interface screen of a corresponding medical device, to receive an indication of user selection of one of the representations displayed on the first screen, and to generate a larger screen representation of the interface screen data of the selected representation, wherein both the first screen and the larger screen convey indicators of an alert or alarm with respect to one of the plurality of medical devices, wherein the representations of the interface screen data from the plurality of medical devices are miniature screen shots or live feeds of screens displayed on the medical devices.

8. The medical device interface system of claim 7, wherein the first screen comprises an indication of a status of a disposable kit for the medical device.

9. The medical device interface system of claim 7, wherein the processing circuit is further configured to implement a command component configured to multi-cast a single command over the communication channel to place a plurality of the medical devices into a mode.

10. The medical device interface system of claim 7, wherein the first screen comprises an indication of an amount of drug dispensed by a medical device.

11. A medical device interface system comprising a processing circuit configured to implement:
    a communication channel configured to communicate with a plurality of medical devices, the medical devices selected from a group consisting of a blood processing instrument, an infusion pump, and a drug delivery system, to receive interface screen data for each of the plurality of medical devices;
    a processing component configured to generate a screen comprising screen shots or live feeds of interface screen data from a plurality of the medical devices, each screen shot or live feed to convey information shown on a respective interface screen of a corresponding medical device, to receive an indication of user selection of one of the screen shots or live feeds displayed on the first screen, and to generate a larger screen representation of the interface screen data of the selected screen shot or live feed, the processing component further configured to receive through the communication channel an indication of an alert or alarm associated with each of a plurality of the medical devices, the processing component configured to automatically rearrange the screen shots or live feeds of interface screen data based at least in part on the received indication of the alerts or alarms.

12. The medical device interface system of claim 11, wherein the screen comprises multiple separately-viewable portions, each portion comprising representations of interface screen data from the plurality of medical devices, the processing component configured to allow a user to move between the multiple portions based on user input, the processing component further configured to receive through the communication channel an indication of an alert or alarm associated with one of the medical devices, the processing component configured to automatically adjust the screen to show the portion having the alert.

13. The medical device interface system of claim 11, wherein the processing circuit is further configured to receive through the communication channel an indication of an alert or alarm having a different priority than the alert or alarm, wherein the processing component is configured to automatically adjust the screen to show the portion displaying the medical device having a higher priority alert or alarm.

14. The medical device interface system of claim 11, wherein the first screen comprises an indication of a status of a disposable kit for the medical device.

15. The medical device interface system of claim 11, wherein the processing circuit is further configured to implement a command component configured to multi-cast a single command over the communication channel to place a plurality of the medical devices into a mode.

16. The medical device interface system of claim 11, wherein the processing circuit is further configured to implement a command component configured to multi-cast a single command over the communication channel to place a plurality of the medical devices into a mode, wherein the system further comprises at least one of a blood processing instrument, an infusion pump, and a drug delivery system.

\* \* \* \* \*